(12) United States Patent
Sadygov et al.

(10) Patent No.: US 7,595,485 B1
(45) Date of Patent: Sep. 29, 2009

(54) DATA ANALYSIS TO PROVIDE A REVISED DATA SET FOR USE IN PEPTIDE SEQUENCING DETERMINATION

(75) Inventors: Rovshan Goumbatoglu Sadygov, San Jose, CA (US); Andreas Huhmer, Mountain View, CA (US)

(73) Assignee: Thermo Finnigan LLC, San Jose, CA (US)

( * ) Notice: Subject to any disclaimer, the term of this patent is extended or adjusted under 35 U.S.C. 154(b) by 365 days.

(21) Appl. No.: 11/703,941

(22) Filed: Feb. 7, 2007

(51) Int. Cl.
*H01J 49/00* (2006.01)
*G01N 21/31* (2006.01)

(52) U.S. Cl. .................. 250/282; 250/281; 250/293; 702/27; 702/28; 435/4; 435/6; 436/173

(58) Field of Classification Search .................. 250/281, 250/282, 283, 284, 286, 287, 288, 290, 291, 250/292, 293; 702/19, 20, 22, 27, 28, 21, 702/23, 24, 25, 26, 29, 30; 435/4, 6, 89, 435/91.1; 530/350; 514/2; 436/173
See application file for complete search history.

(56) References Cited

U.S. PATENT DOCUMENTS

| | | | |
|---|---|---|---|
| 6,745,133 B2 | 6/2004 | Axelsson | |
| 2002/0001814 A1* | 1/2002 | Chu et al. | 435/7.1 |
| 2002/0090637 A1* | 7/2002 | Stroobant | 435/6 |
| 2003/0129760 A1 | 7/2003 | Aguilera et al. | |
| 2003/0236636 A1 | 12/2003 | Yoshinari et al. | |
| 2004/0143402 A1 | 7/2004 | Colinge et al. | |
| 2005/0199804 A1* | 9/2005 | Hunt et al. | 250/290 |
| 2005/0221500 A1 | 10/2005 | Reid et al. | |
| 2006/0004525 A1* | 1/2006 | Washburn et al. | 702/19 |

(Continued)

FOREIGN PATENT DOCUMENTS

WO   WO 2004/063215 A2   7/2004
WO   WO 2004/063215 A3   7/2004

OTHER PUBLICATIONS

Sadygov et al., "Code Developments to Improve the Efficiency of Automated MS/MS Spectra Interpretation", Journal of Proteome Research, May 2002 vol. 1(3), pp. 211-215.*

(Continued)

*Primary Examiner*—Jack I Berman
*Assistant Examiner*—Nicole Ippolito Rausch
(74) *Attorney, Agent, or Firm*—Sharp Upham; Thomas F. Cooney (57) ABSTRACT

In one aspect of the present invention, the less "useful" spectral data is disregarded from the spectral data resulting from the fragmentation by ETD and candidate charge states for the "useful" data assigned. Knowledge of the first order ion product charge state reduces the subset of comparison data hence aiding in the eventual identification of the precursor ion, and thus aiding in peptide sequence database searching capabilities. Such capabilities include, but are not limited to, computational requirements for database search and data storage, CPU time, the volume taken up on the hard disk to store results, visualization and dissemination of data, and overall improvement in the confidence in the precursor identification. Thus determination of the peptide sequence can be resolved in less time, costing less money, and requiring less computer power.

24 Claims, 8 Drawing Sheets

U.S. PATENT DOCUMENTS

2006/0186331 A1* 8/2006 Hartmer et al. ............. 250/288
2006/0255259 A1* 11/2006 Zubarev et al. ............. 250/282
2007/0122864 A1* 5/2007 Woods et al. ................. 435/23
2008/0167824 A1* 7/2008 Reinhold et al. ............. 702/27
2008/0286764 A9* 11/2008 Geromanos et al. ........... 435/6

OTHER PUBLICATIONS

Schutz et al., "Deriving Statistical Models for Predicting Peptide Tandem MS Product Ion Intensities," Biochemical Society Transactions, vol. 31 ( No. 6), p. 1479-1483, (2003).

Good et al., "Advancing Proteomics with Ion/Ion Chemistry," Mass Spectrometry for Proteomics Analysis Review, vol. 40 ( No. 6), p. 783-788, (2006).

Macek et al., "Top-down Protein Sequencing and MS3 on a Hybrid Lnear Quadrupole Ion Trap-Orbitrap Mass Spectrometer," Molecular & Cellular Proteomics 5.5, American Society for Biochemistry and Molecular Biology, Inc., p. 949-958, (2006).

Huang et al., "The Influence of Histidine on Cleavage C-Terminal to Acidic Residues in Doubly Protonated Tryptic Peptides," Int'l J. Mass Spectrometry, p. 233-244, (2002).

Huang et al., "Dissociation Behavior of Doubly-Charged Tryptic Peptides: Correlation of Gas-Phase Cleavage Abundance with Ramachandran Plots," J. Am. Chem. Soc., vol. 126 ( No. 10), p. 3034-3035, (2004).

Gibbons et al., "SILVER Helps Assign Peptides to Tandem Mass Spectra Using Intensity-Based Scoring," J. Am. Soc Mass Spectrom, vol. 15, p. 910-912, (2004).

Jimmy K. Eng et al., "An Approach to Correlate Tandem Mass Spectral Data of Peptides with Amino Aciid Sequences in a Protein Database," J Am Soc Mass Spectrom 1994, 5, pp. 976-989.

Joshua J. Coon et al., "Anion Dependence in the Partitioning between Proton and Electron Transfer in Ion/Ion Reactions," International Journal of Mass Spectrometry 236 (2004), pp. 33-42.

\* cited by examiner

DATA ANALYSIS TO PROVIDE A REVISED DATA SET FOR USE IN PEPTIDE SEQUENCING DETERMINATION

FIELD OF THE INVENTION

The invention relates to a method for analyzing product ion data to produce a revised data set that can be used in peptide sequencing determination. More specifically, the invention relates to determining the charge states of product ions generated from precursor ions by a non-ergodic technique.

BACKGROUND OF THE INVENTION

Mass spectrometry has become the method of choice for fast and efficient identification of proteins in biological samples. Tandem mass spectrometry of peptides in a complex protein mixture can be used to identify and quantify the proteins present in the original mixture. Tandem mass spectrometers achieve this by selecting single m/z values and subjecting the precursor ions to fragmentation, providing product ions that can be used to sequence and identify peptides. The information created by the product ions of a peptide can be used to search peptide and nucleotide sequence databases to identify the amino acid sequence represented by the spectrum and thus identify the protein from which the peptide was derived. To identify peptides, database searching programs typically compare each MS/MS spectrum against amino acid sequences in the database, and a probability score is assigned to rank the most likely peptide match. The algorithms typically utilize mass-to-charge ratio (m/z) information for identification purposes of the various product ions.

Fragmentation can be provided by various methodologies and mechanisms. Ion activation techniques that involve excitation of protonated or multiply protonated peptides, include collision-induced dissociation (CID), and infrared multiphoton dissociation (IRMPD) for example, and have been used to identify sequences. In these dissociation methods translational energy is imparted to the peptide and is converted into vibrational energy that is then distributed throughout the bonds of the peptide. When the energy imparted to a particular bond exceeds that required to break the bond, fragmentation occurs and product ions are formed. The cleavage may not always however, occur along the backbone of the peptide if, for example, the side-chain of the peptide has elements that inhibit cleavage along the backbone, by providing a lower energy pathway and cleavage site on a side-chain. This preferential cleavage of the side-chain bonds rather than the polypeptide bonds often results in the provision of information primarily about the side-chain sequences and not the peptide sequence.

Other mechanisms of fragmentation include for example, those in which the capture of a thermal electron is exothermic and causes the peptide backbone to fragment by a non-ergodic process, those that do not involve intramolecular vibrational energy redistribution. Such methodologies include Electron Capture Dissociation (ECD) and Electron Transfer Dissociation (ETD). ECD and ETD occur on a time scale that is short compared with the internal energy distribution that occurs in the CID process, and consequently, most sequence specific fragment forming bond dissociations are typically randomly along the peptide backbone, and not of the side-chains.

Though non-ergodic reactions such as ETD or ECD fragmentation appear to offer the best solutions for peptide determination, these techniques create their own problems. ECD can not be performed with trap-type mass analyzers since the electrons created by the reaction do not typically retain their thermal energy long enough to be trapped, thus ECD is typically performed on a FT-ICT mass spectrometer. These instruments are expensive. ETD fragmentation particularly of large peptides and proteins, which can be performed by an ion trap, often leads to spectra too complicated for direct interpretation. Typically, these larger peptides are highly charged, and their fragment ions are similarly multiply charged, with charge states of +2, +3, +4, +5, +6 and even +7 observed. The limited m/z resolution of currently available mass analyzers makes interpretation of these highly charged product m/z spectral data difficult. In addition, the charge state determination is more complicated and important than for CID where normally charge states up to only +4 are observed.

A precursor subjected to the ETD fragmentation process fragments mainly along its backbone, generating predominantly fragments of the precursor ion. However, in addition to the fragment ions, peaks are generally seen for ions which have been subjected to neutral loss, such as water (−18 Da) for example. Ions from side chain cleavage are generally not observed. Despite the absence of side chain cleavage, the spectral data obtained via the ETD process is typically possesses spectral information that may contain little or no "useful" information in terms of peptide sequencing or identification.

For large peptides and proteins, and the large number of possible charge states, the number of possible matches in a database is also larger. For example, if the precursor ion has a charge state of +3, each fragment of the precursor found in the MS/MS or MSN spectral data can have a possible charge state of +3, +2 or +1. Since it is not possible to directly determine the charge state of each of the fragments in a MS/MS spectrum (the spectrum only provides mass to charge ratio information), if the precursor ion is not known, several searches must be performed. In this case, separate searches considering possible +3, +2 and +1 precursor ion charge states may need to be performed. This is consuming in terms of time and space, in terms, for example, of computer storage space, the number of searches performed, computer execution time, and the valuable time of the scientist in reviewing the data.

SUMMARY

In one aspect of the present invention, the less "useful" spectral data is disregarded from the spectral data resulting from the fragmentation by a non-ergodic reaction such as ETD, and candidate charges for the "useful" data are assigned. To facilitate this, first order ion products and second order ion products are identified. Knowledge of the product ion charge reduces the subset of comparison data hence aiding in the eventual identification of the precursor ion, and thus aiding in peptide sequence database searching capabilities. Such capabilities include, but are not limited to, computational requirements for search requirements and data storage such as the CPU time taken in searching, the volume taken up on the hard disk to store large quantities of search results for redundant charge states, visualization and dissemination of data, and overall improvement in the confidence in the precursor identification. Thus allowing the determination of the peptide to be determined in less time, costing less money, and requiring less computer power.

Less "useful" spectral data may comprise data considered to be below a certain threshold, that threshold being that of the noise level, or not sufficient data above a minimum threshold in terms of peaks above the threshold level. Less "useful" data may also comprise data that is defined as a second order ion product rather than a first order ion product.

Analysis of the "useful" data may comprise utilizing not only the first order ion product data, but also the second order ion product data as part of the analysis process.

In another aspect of the present invention, a storage medium encoded with machine-readable computer program code is provided, the storage medium including instructions for identifying the first and second ion products from the spectral data resulting from the fragmentation by a non-ergodic reaction such as ETD. The instruction enabling less "useful" spectral data to be disregarded and candidate charges for the "useful" data to be assigned.

These and other aspects of the invention will become apparent from the following description. In the description, reference is made to the accompanying drawings that form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE DRAWINGS

FIG. 7 illustrates experimental product ion spectral data, and shows what a typical +2 spectrum may look like.

Like reference numerals refer to corresponding parts throughout the several views of the drawings.

DETAILED DESCRIPTION OF EMBODIMENTS

The present invention addresses some of the shortcomings of the known art. A method for determining the charge states of product ions generated from precursor ions by a non-ergodic technique such as ETD or ECD is provided in one aspect of the invention. In another, an improved method for determining the charge state of a precursor ion for use in peptide sequencing determination is also provided.

Before describing the invention in detail, a few terms that are used throughout the description are explained. As used in this specification, a peptide or polypeptide is a polymeric molecule containing two or more amino acids joined by peptide (amide) bonds. As used in this specification, a peptide typically represents a subunit of a parent polypeptide, such as a fragment produced by cleavage or fragmentation of the parent polypeptide using known techniques. Peptides and polypeptides can be naturally occurring (e.g., proteins or fragments thereof) or of synthetic nature. Polypeptides can also consist of a combination of naturally occurring amino acids and artificial amino acids. Peptides and polypeptides can be derived from any source, such as mammals (e.g., humans), plants, fungi, bacteria, and/or viruses, and can be obtained from cell samples, tissue samples, bodily fluids, or environmental samples, such as soil, water, and air samples.

Figure 1:
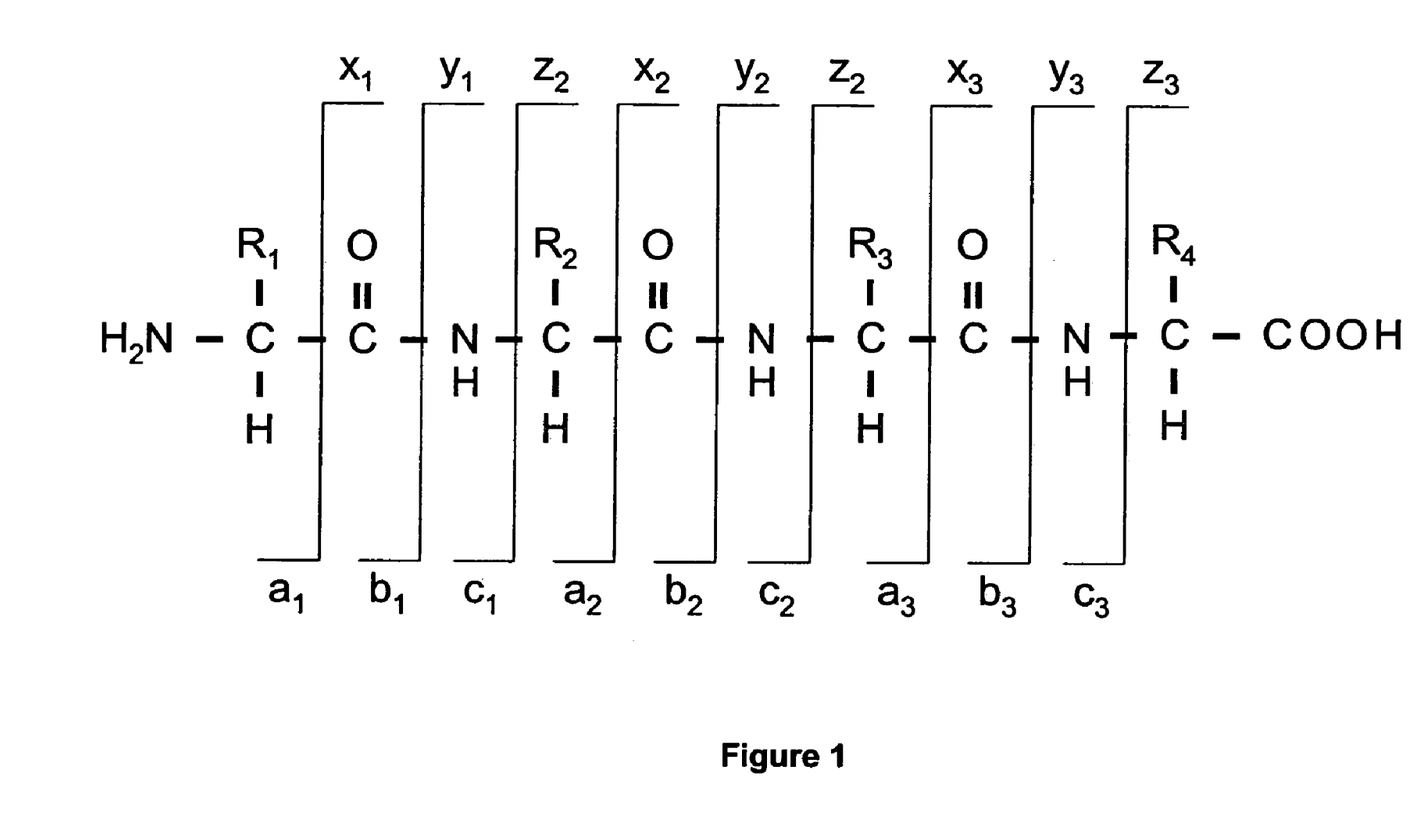
FIG. 1 depicts a nomenclature typically adopted for the fragment of peptides and proteins.

A nomenclature typically adopted (and used herein) for the fragments of peptides and proteins has been suggested in the literature and is depicted in FIG. 1. The three possible cleavage points of the peptide backbone are called a, b and c when the charge is retained at the N-terminal fragment of the peptide and x, y and z when the charge is retained by the C-terminal fragment. The numbering indicates, which bond is cleaved counting from the N- and the C-terminus respectively, and thus also the number of amino acid residues in the fragment ion. The number of hydrogen atoms transferred to or lost from the fragment is indicated with apostrophes to the right and the left of the letter respectively.

Electron transfer dissociation (ETD) is a non-ergodic process, a unimolecular dissociation that yields product ions that represent cleavages between most of a peptide's or protein's amino acids. ETD produces mainly c and z* fragment ions (ion products) and to a much smaller extent a*, y ions and z' and c* ions. The ETD process generally results in almost complete sequence coverage for small peptide ions, with the exception of dissociation of N-terminal residues of proline, which unlike the case for all other amino acids, requires dissociation of two bonds.

For a productive ETD experiment multiply-charged peptide cations are reacted with an electron transfer reagent to initiate the dissociation of the cation yielding sequence specific ion products according to equation (1).

$$[M+nH]^{n+} + A^{-*} \rightarrow [C+(n-m)H]^{(n-m-1)+} + [Z+mH]^{m+} + A \quad (1)$$

where $A^{-*}$ is the electron transfer reagent, the $[M+nH]^{n+}$ is the cation and the $[C+(n-m)H]^{(n-m-1)+}$ and $[Z+mH]^{m+}$ are the c and z* type fragment ions, respectively.

The reaction of the electron transfer anion proceeds through both electron transfer (with and without dissociation) and proton transfer (without dissociation). Electron transfer reactions that proceed with dissociation give rise to cleavage along the peptide backbone, loss of neutral molecules and cleavage of the Cysteine bond (if present), these are first order ion products.

ETD, therefore, is a process of three competing reactions, one of which yields the desired product ion representing sequence specific information (second order ion products), while the other reaction pathways yield product ions that provide no specific information about the amino acid sequence of proteins or peptides.

A competing side reaction pathway for the creation of fragment ions in reaction pathway (1) is the proton transfer reaction according to equation:

$$[M+nH]^{n+} + A^- \to [M+(n-1)H]^{(n-1)+} + AH \quad (2)$$

where $A^-$ is the transfer reagent.

Another competing side reaction pathway without first order ion product formation is the anion attachment according to equation (3):

$$[M+nH]^{n+} + A^- \to [M+nH+A]^{(n-1)+} \quad (3)$$

where $[M+nH+A]^{(n-1)+}$ is the anion adduct.

Conversion of the precursor cation into desired first order product ions is highly dependent on the ion-ion reaction conditions chosen in the experiment and are variable with the choice of anion reagent, reaction temperature, nature of carrier gas, gas pressure etc.

The ETD technique produces low energy electrons that are captured by multiply-protonated species that transforms the precursor ion from an even-electron closed-shell system to an odd-electron hypervalent system that deposits the energy associated with the electron capture in to the precursor ion. The desired reaction pathway is the electron transfer reaction, which transforms the precursor ion into an energetically excited, first order ion according to equation (4):

$$[M+nH]^{n+} + A^{-*} \to [M+nH]^{(n-1)+*} + A \quad (4)$$

that then proceeds to dissociate into sequence specific product ions. The desired product ions are the result of a unimolecular dissociation of the excited first order ion product intermediate according to equation (5):

$$[M+nH]^{*(n-1)+*} \to [C+(n-m)H]^{(n-m-1)+} + [Z+mH]^{m+*} \quad (5)$$

However, first order ion products can undergo sequential reactions that lead to higher-order charge reduced ions of the precursor cation and, in extreme cases, to the neutralization of the precursor. In these cases the ion-ion reaction leads to the reduction of charge without any dissociation into first order ion products according to equation (6):

$$[M+nH]^{(n-1)+*} + A^{-*} \to [M+nH]^{(n-2)+**} + A \quad (6)$$

Similarly, the successive transfer of a proton from the excited intermediate to the anion reagent can lead to the formation of charge reduced species without dissociation into second order fragment ions according to equation (7):

$$[M+nH]^{(n-1)+*} + A^{-*} \to [M+(n-1)H]_{(n-2)+} + AH \quad (7)$$

The successive reaction of the first order product ion with electron transfer reagent can lead to a number of ioon reaction products that can be comprised of a mixture of species formed exclusively by proton transfer or electron transfer reactions or a mixture of both electron and proton transfer reactions. It is to be noted that the exact charge state and compositional nature of these ion products are usually difficult to determine without use of a high resolution mass spectrometer. Unit resolution mass spectrometers can not distinguish between the different isobaric species of the first order ion-ion products resulting from the successive reaction of the first order ion product with electron transfer reagent.

It has been shown previously that the precursor cation charge state plays a major role in determining the extent of electron transfer and the dissociation products observed resulting from reactions with anions. That is, the ion-ion reaction of the more highly charged cations is inherently more exothermic than the reaction of the same peptide at lower charge state. It can be expected that the difference in reaction exothermicity not only influences the reaction rate and quantity of the first order ion products, but also the nature and products of the successive dissociative and non-dissociative products. Furthermore, the kinetic stability of the first order ion products differ as the ion products experience greater electrostatic repulsion with increase in precursor ion charge state. To the extent that the electrostatic repulsion reduces the dissociation barriers for the second order ion products, it can be expected that ion product dissociation rates will greatly increase with charge. Conversely, reaction rates associated with the formation of non-dissociative first order ion products will decrease accordingly. It is the charge state and the compositional nature of the precursor cation that ultimately determines the preferences of the diverse reaction channels leading to first order dissociative and non-dissociative ion products and their quantity.

The transfer of an electron to the precursor ion is a highly exothermic reaction that produces localized excitation that yields dissociation of the precursor into product ions or the loss of neutral side chains. Usually, more than 80% of all cleavages observed in ETD are of the c and z* type; however, other fragmentation channels include losses of small molecules and radicals from the first order reduced species. Those losses constitute approximately less than 10% of all ion products and do not make any sequence specific information available, but provide information about the charge state (electronic state) and nature of their precursors. Several different neutral loss species can be identified in ETD spectra such as, for example a loss of 17 amu ($NH_3$), a loss of 44 amu (from either $CO_2$ or $CH_4N_2$, the latter being a portion of an Arginine side chain), losses of 42 amu (NH—C—NH) and 59 amu (($H_2N)_2C$=NH) from portions of Arginine side chains, a loss of 45 amu ($CH_3NO$) from portions of Asparagine and Glutamine side chains, losses of 72 amu (—($CH_2)_4$—$NH_2$) and 73 amu ($C_4H_{11}N$) from Lysine side chain losses, and losses of 74 amu ($C_3H_6S$), 82 amu ($C_4H_6N_2$) and 101.095 amu ($C_4H_{11}N_3$) originating, respectively, from losses of Methione, Histidine and Arginine side chains. The observed neutral losses are predominantly associated with neutral losses from first order ion products.

Similarly, adducts can form from intermediate excited states that give clues about the electron state and nature of its precursor. In particular z* ions have the tendency to form adducts, such as molecular oxygen adducts (z+32 amu) as well as hydroxyl adducts (z+17 amu).

Having explained the meaning of a few terms that have been used in describing the invention, the broad concepts of the invention will now be explained with the aid of FIGS. 2-5. FIGS. 6-11 illustrate how the invention can be utilized to determine the candidate charge states of the first order ion products, and hence enable and improve the peptide searching capabilities.

Figure 2:
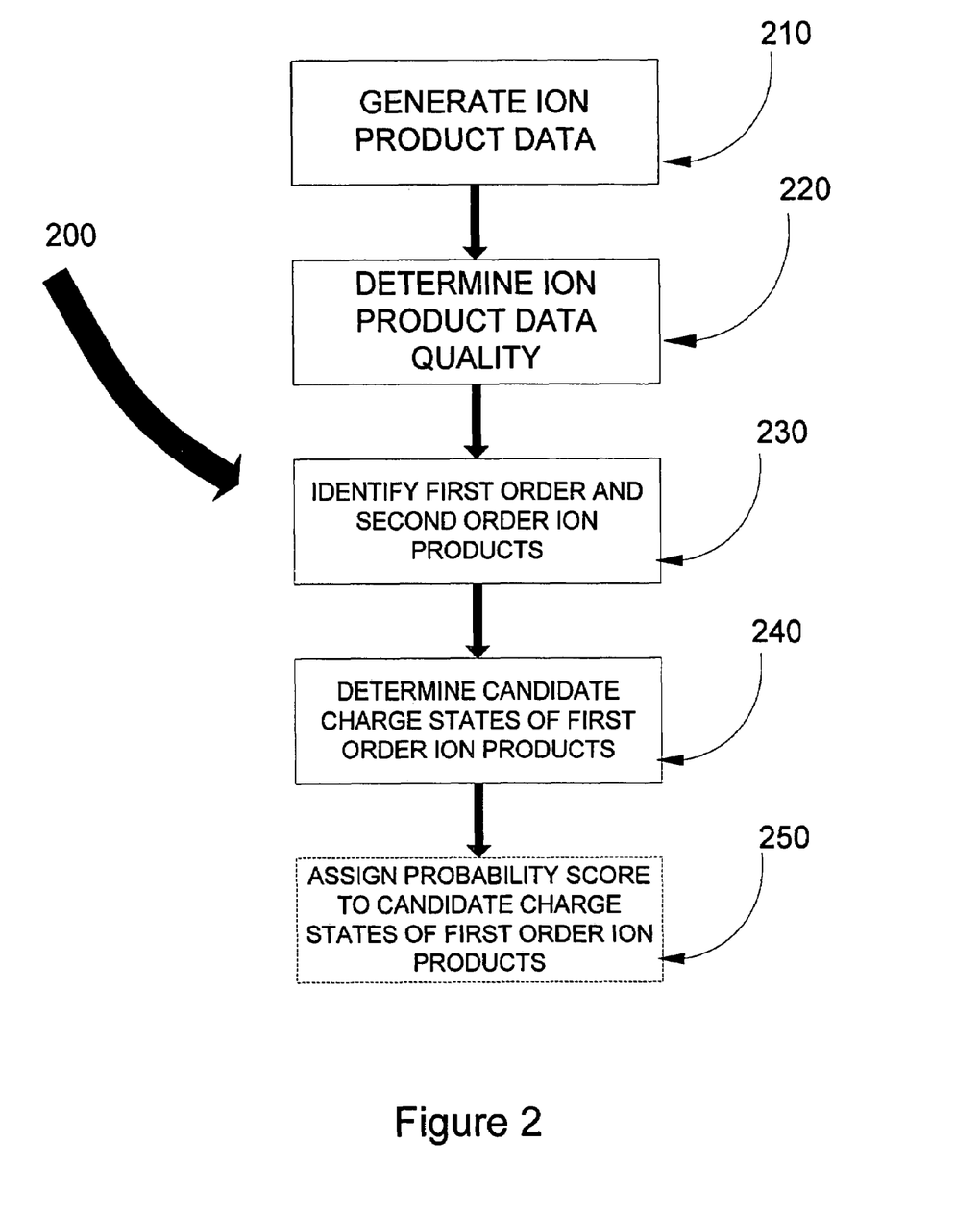
FIG. 2 is a flowchart illustrating the steps that are performed in order to assign a probability score to the candidate charge states of the first order ion products, in accordance with an aspect of the present invention.

FIG. 2 is a flowchart 200 depicting the steps for analyzing product ion data to produce a revised data set that can be used in peptide sequencing determination. As shown in FIG. 2, step 210 relies on the fact that ion product fragments have already been generated by a non-ergodic fragmentation process. Non-ergodic fragmentation processes include, but not limited to electron capture dissociation (ECD) or electron transfer dissociation (EDT), processes which as discussed briefly in the Background Section, above, and known to those in the art, do not involve intramolecular vibrational energy redistribution.

Once generated, the fragments of a precursor ion may include products such as, but not limited to, charge reduced precursors, electron transfer products, anion adducts, side chain losses, hydrogen transfer products, fragment ions, products of fragment ion adducts and products of fragment ion neutral losses. Therefore, the spectral data representative of the fragments contains not only first order ion products which have come directly from the fragmentation of the intact and charged precursor, but second order ion products which are the results of fragmentation of the first order ion products. Furthermore, higher order ion products can also be present, adding further to the difficulty in peptide sequence identification.

Having generated the fragments of the precursor ion, ion product data is generated in Step 210, via some analysis mechanism such as an ion trap mass analyzer for example, a three-dimensional ion trap, a two-dimensional ion trap, or an orbitrap mass analyzer. In some instances, fragmentation and ion product data generation may occur in one instrument such as a mass analyzer, in other instances this may be a two step process, generating the fragments in one instrument, and then transferring them to another to obtain the mass spectral data, the ion product data. The fragmentation of precursor ions and the generation of ion product data from the fragments produced are known to those skilled in the art, and are not discussed in detail herein. Typically, ion product data comprises spectra of intensity/abundance vs. mass-to-charge ratio, though other forms of spectra fall within the scope of the invention.

Having generated ion product data, the ion product data is subjected to various type of data analysis. The analysis may be performed on data from a single spectrum, or data from a combined number of spectra. Using data from a number of spectra may enable any errors that may exist to be reduced, and/or may enable the user to identify fragments in one scan that may not have been present or not present in sufficient abundance in another scan.

In one aspect of the invention, the aim is to analyze the ion product data such that charge states can be assigned to the useful peaks. Useful peaks are typically associated with charge-reduced precursors, electron transfer products, anion adducts, side chain losses and hydrogen transfer products. Once charge states have been assigned to the useful peaks, a reduced set of data can thus be generated prior to searching a database for matches to the spectra to obtain the molecular weight of the original precursor. The revised data set may be further reduced by utilizing a probabilistic method to assign a probability score to the each of the useful peaks, and subsequently utilizing the highest probability scoring useful peak to aid in the search for possible matches in a database. Hence providing for an improved peptide sequence database capability in identifying a probable precursor. The improved capability being not only in terms of time and cost savings, but in improved confidence in the results obtained, for example.

The data analysis may be carried out by means of a storage medium encoded with machine-readable computer program code. For example the data analysis may be carried out by a computer system comprising for example a central processing unit (CPU), memory, display and various additional input/output devices. Such a data analysis system may form part of the overall mass analyzer or be a separate stand alone unit, connected to the mass analyzer through input/output interfaces known in the art. Those in the art will also appreciate that the series of computer instructions that embody the functionality described hereinbefore can be written in a number of programming languages for use with many computer architectures and numerous operating systems.

The first step of analysis, step 220, is to determine the quality of the ion product data, ensuring the data is of a predetermined quality before further processing. This step, in its lowest form of analysis, disregards the intensity/abundance values below some threshold value, typically the "noise" threshold value. For example, the quality of ion product data may be considered to fall below a threshold if the spectral peaks are not of an intensity/abundance value of 0.0001% of the precursor abundance value. In this instance of the present invention, it may be deduced that since the minimum quota of data above the "noise" threshold is not met, there is not sufficient data to enable one to utilize for peptide sequencing purposes. In this instance, the process can be stopped, ensuring that valuable user and CPU time is not wasted.

In other forms, the quality determination is based on a requirement for a minimum quota of data above a threshold value. For example, in another aspect of the invention, data may be considered to be below the threshold if there are fewer than ten, twenty, thirty, forty or fifty spectral peaks over half a spectral range, the spectral range being the range over which the product data was originally generated. In a further aspect of the invention, data may be considered to be below the threshold if there are fewer than twenty, thirty, forty, fifty or sixty peaks after the precursor ion mass-to-charge ratio value over the whole spectral range. In yet a further aspect of the invention, even though there may be sufficient peaks either over half a spectral range or after the precursor, the peaks may not be above the "noise" level, and hence still be considered to fall below the desired threshold. Those skilled in the art should appreciate that although numbers such as ten, twenty, thirty, forty, fifty and sixty have been utilized, these are representative of any number, and will depend on the size of the precursor ion, type of precursor ion, fragmentation method, apparatus used, contamination, internal, external and various other conditions and influences, the number effectively dictated by the user typically combined with experimentation and/or experience/teachings.

Typically, when it is determined that the predetermined quality of the ion product data is below a threshold value, it may be concluded that the ion products generated are not useful for peptide sequencing purposes. Alternatively, it may be possible that there is sufficient information to ascertain that the only possible candidate charge state of any observed intensity peak is +2. When it is determined that the predetermined quality of the ion product data is above a threshold value, it may be concluded that the ion product generated is useful for peptide sequencing purposes, and it may be assigned a charge state of greater or equal to +2, such as +2, +3, +4, +5, +6 or +7 for example.

The second step of analysis, step 230, is to identify portions of the predetermined quality ion product data (above the threshold) that represent first order and second ion products. These portions of the ion product data may comprise the presence or the absence of at least one spectral peak. The fragments generated by the ETD process typically include charge reduced precursors, electron transfer products, anion adducts, side chain loses, hydrogen transfer products, fragment ions, products of fragment ion adducts and products of fragment ion neutral loses. As explained earlier, first order ion products are the reduced charge state ion products, the electron transfer ion products, hydrogen transfer ion products, or adduct ion products. Second order ion products are any product that is the result of a true dissociation reaction forming sequence specific fragments. In this step, precise identification of the spectral peak that is associated to a charge reduced precursors, electron transfer product, anion adduct, side chain loss, hydrogen transfer product, fragment ion, product of a fragment ion adduct or product of a fragment ion neutral loss is not required, though may be useful. At this stage of the process, there is a need to differentiate between first order ion products and second order ion products; to differentiate between the first order ion products which may include fragments including charge reduced precursors, electron transfer products, anion adducts, side chain loses and hydrogen transfer products, and second order ion products which may include fragments including fragment ions, products of fragment ion adducts and products of fragment ion neutral loses. Once differentiated, the first order ion products are the ones that generally provide the most useful information in terms of precursor ion identification, and the eventual peptide sequence determination. By differentiating between the first and second ion products, one may therefore be able to revise, and typically reduce the data set prior to further processing. In addition, the ratio of the first and higher order ion products is indicative of the efficiency of the ETD fragmentation process, a lower ratio indicating that the ion product data generated is not useful for peptide sequencing purposes.

Having now revised, and typically reduced this data set, in step 240, candidate charge states are determined for each of the first order ion products. This determination is typically carried out by analysis of the data, the analysis utilized comprising techniques that utilize at least one of peak abundance, peak position, peak density, peak spacing, peak presence or peak absence. This step can be simple or extremely complex depending upon the initial precursor ion, its size and type, the fragmentation method employed, the apparatus used, contamination, internal, external and various other conditions and influences. In one aspect of the present invention (depicted in a later figure as step 305), the fragments comprising the second order ion products are utilized to determine the candidate charge state of the first order ion products. This may be achieved by, for example, firstly identifying the complementary second order ion products (complementary to the first order ion products), and then applying a Fast Fourier Transform to the complementary second order ion products. If it fits, the candidate charge state of the first order ion product can be determined. Alternatively, the degree of fit may be taken into account in a probabilistic method employed to assign a probability score to the candidate charge state. Other possible methods that can be used for candidate charge state determination of the first ion product shall be discussed in greater detail in connection with FIGS. 2-4 later.

At this point, the candidate charge states have been determined and a revised data set has been generated, one in which not only data that falls below a desired threshold is disregarded, but one in which first and second order ion products have also been identified. This revised data set is typically a reduced data set, data that is reduced in size compared to the fragmentation data originally generated by the ETD process. Consequently further processing of this revised data set can only improve peptide sequence database searching, reducing for example the CPU time required, computer storage space needed, the number of searches that need to be performed, computer execution time, and the valuable time of the scientist in reviewing the data.

Although an aspect of the present invention can be illustrated by steps 210, 220, 230 and 240 of FIG. 2, in another aspect of the present invention, additional value can be attained by step 250 which employs a probabilistic method to assign a probability score to the candidate charge states of the first order ion products. Assignment of such a score enables the most likely candidates to be compared to the database data first, and if a match is found, processing of the less or least likely candidates may not be required. Once again, step 250 provides for a revised data set to be generated. However in this step the revision may not necessarily involve data being disregarded, but being re-ordered, with the most probable occurring in a position within the data set that enables it to be further processed first or at least before the less likely or least likely alternatives. Alternatively, it may be found that certain candidate first ion products are not at all likely, or below a certain threshold of probability, and in this instance the revised data set may also be a reduced data set.

By implementing the method described hereinbefore, one can not only improve peptide sequence database searching by reducing for example the CPU time required, computer storage space needed, the number of searches that need to be performed, and the valuable time of the scientist in reviewing the data, but by also gaining a higher confidence in the results. Having disregarded data that falls below a threshold value, and optionally assigned a probability score to the candidate charge states of the first order ion products, one has reduced the probability of matching fragments that should have been disregarded from fragment spectra in the peptide sequence database. Therefore one has reduced the probability of incorrectly determining the precursor ion and/or the peptide sequence, and increased the confidence of correct assignment. The database searching capabilities have therefore been further improved.

Figure 3:
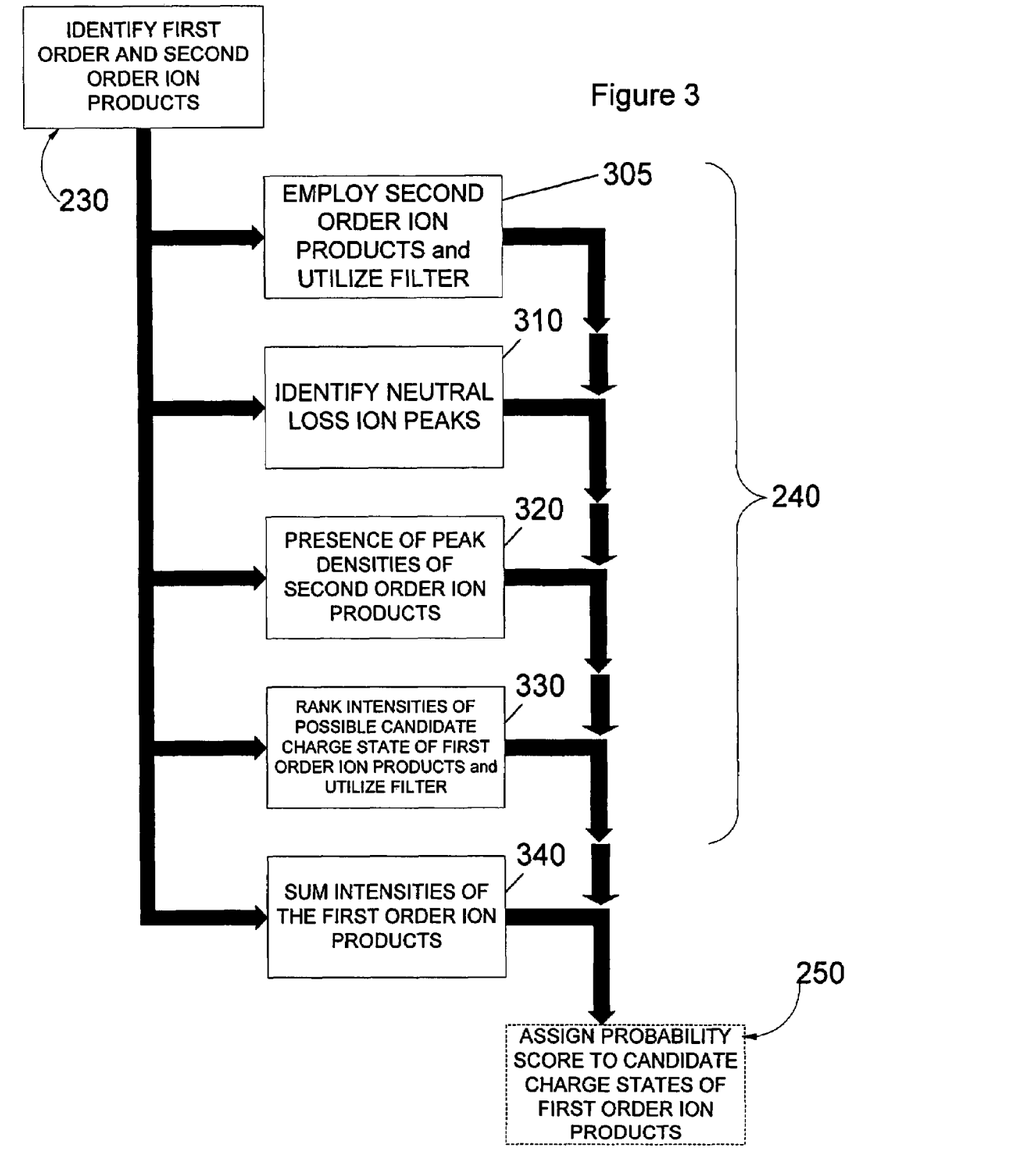
FIG. 3 is a flowchart illustrating the steps that may be performed in order to determine the candidate charge states of the first order ion products, in accordance with one aspect of the present invention.
Figure 4:
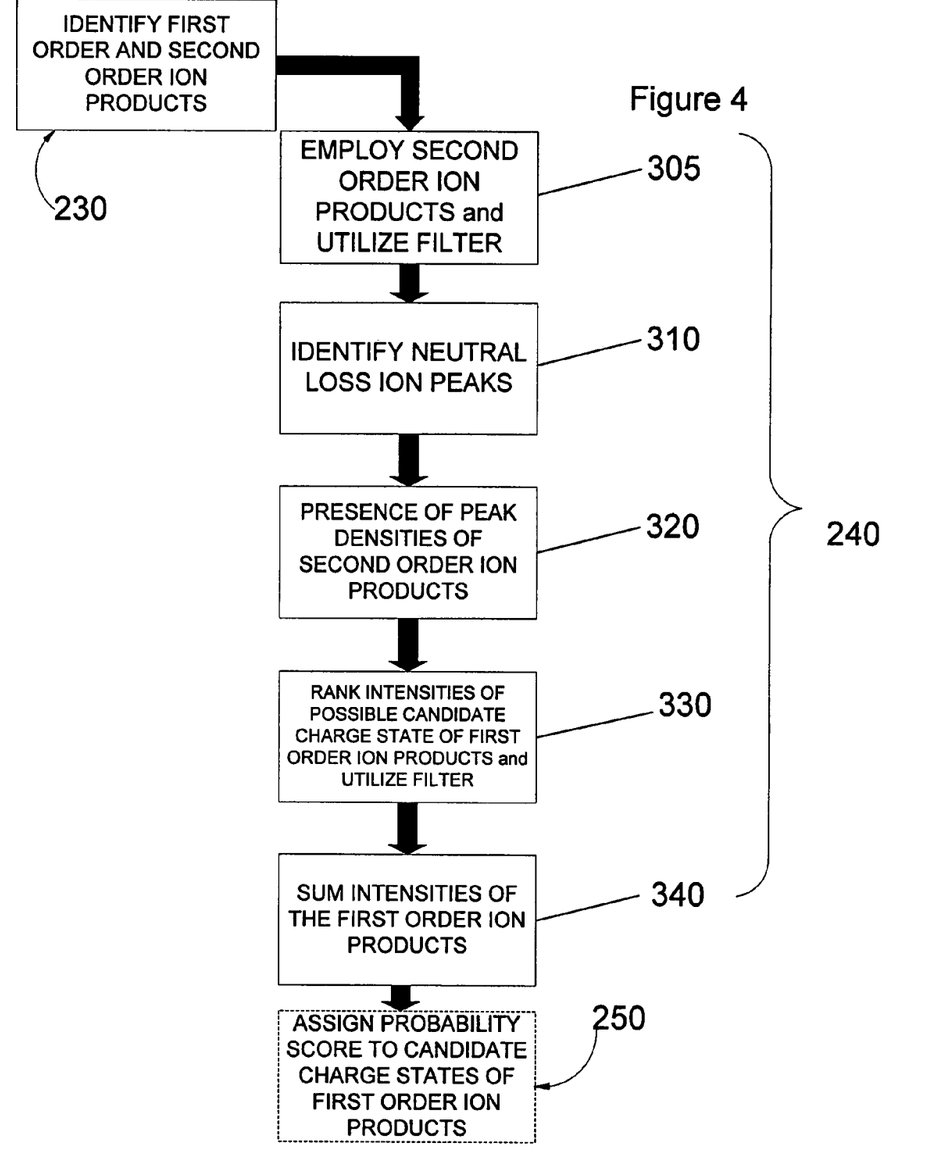
FIG. 4 is a flowchart illustrating the steps that may be performed in order to determine the candidate charge states of the first order ion products, in accordance with another aspect of the present invention.
Figure 5:
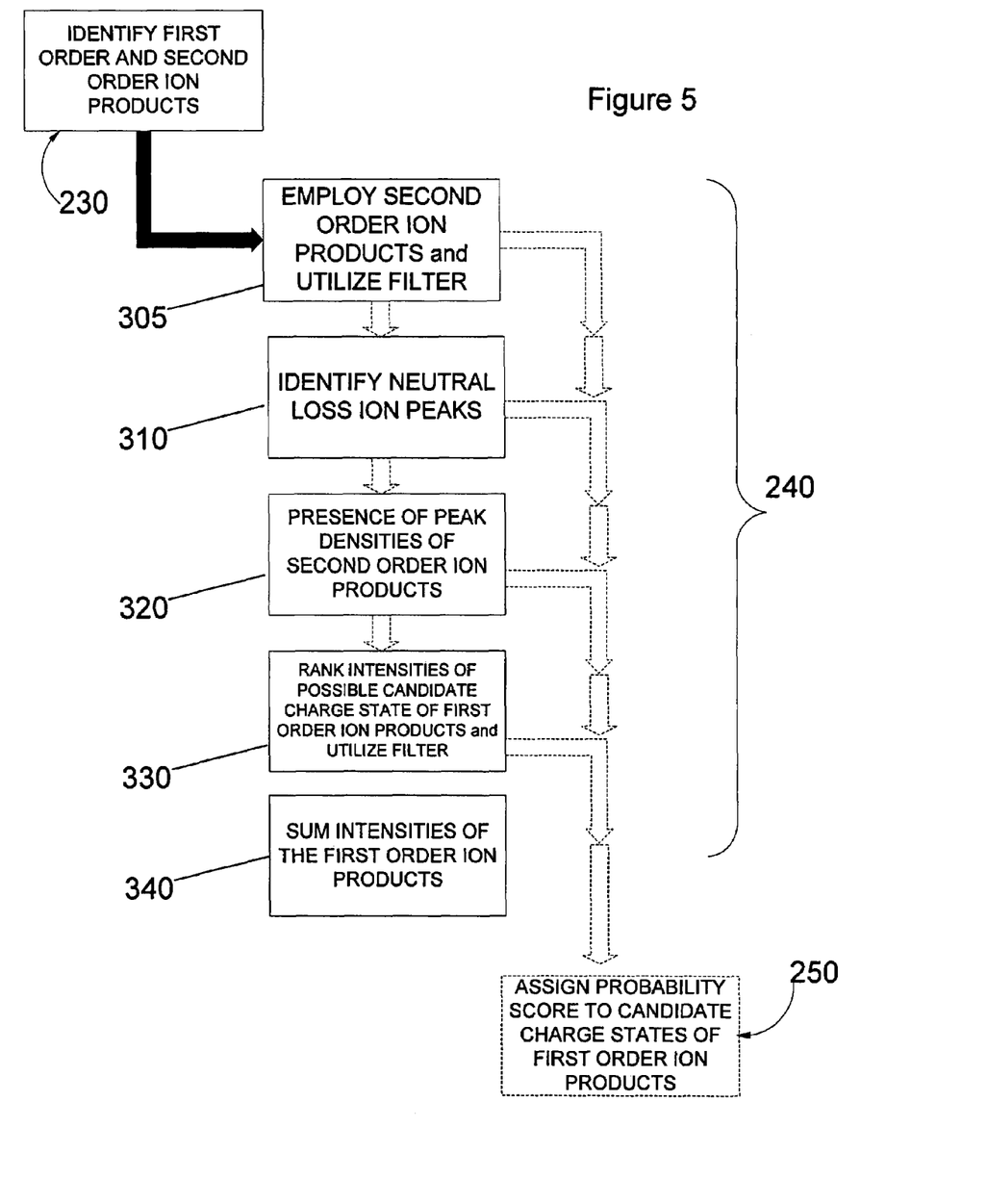
FIG. 5 is a flowchart illustrating the steps that may be performed in order to determine the candidate charge states of the first order ion products, in accordance with yet a further aspect of the present invention.

As mentioned earlier, step 240 dictates that candidate charge states are determined for each of the first order ion products. FIGS. 3-5 illustrate various methods of achieving such a determination. It should be recognized that these methods are presented as examples of how candidate charge determination can be achieved and should not be construed as limiting the invention to a particular mode of operation.

Referring initially to FIG. 3, it can be seen that step 240 has been broken into five distinct steps, identified as steps 305, 310, 320, 330 and 340. As illustrated, these five steps occur simultaneously, and the results of each analysis have to be acquired and combined before the candidate charge state(s) of the product ions can be determined. Although FIG. 3 illustrates that the determination of the candidate charge states of the first order ion products can be achieved in five steps, this number of steps is not intended to limit the scope of the current invention to this number, more steps may be added, or fewer may be employed. The reference numerals have been retained to represent the similar step taken with reference to FIGS. 4 and 5, though it will be apparent later that the methods described do have their differences.

Step 305 was discussed previously, in which the complementary second order ion products were utilized to determine the candidate charge state of the corresponding first order ion product. In step 310, the candidate charge state of the first order ion product is determined by identifying neutral loss ion peaks, utilizing a known mass-to-charge ratio interval between the neutral loss peak and the first order ion product peak. Neutral loss peaks are peaks from radicals or molecules that are lost from an ion to produce an ion of lower mass, for example 17-18 amu representing the loss of $H_2O$ and $NH_3$. Neutral losses represent species that have no charge. The presence of a neutral loss peak adjacent to the first order ion product can be used to distinguish charge states +1 and +2 first order products from higher charged first order products.

In step 320, the candidate charge state of the first order ion product is determined by checking for the presence of peak densities of second order ion products between the first order ion products. This analysis determines if the candidate charge state of a higher value than another charge state should be selected. The presence of a density of second order ion products is useful particularly when consecutive ion states are determined as possible charge states.

In step 330, the determination of the candidate charge state of the first order ion product is determined by utilizing the intensity ratios to distinguish between a higher and a lower possibility of candidate charge state. For example, +2 charge state ion are likely to be in greater abundance than other multiply charged ions, except possibly for the original precursor.

In step 340, the determination of candidate charge state of the first order ion product is determined by summing the intensities of all first order ion products, as the most likely charge state for first order ion product will be the one that yields the highest ion intensity. For example, consider that the candidate charge state of a first order ion product is +4, and the intensity of peaks (in arbitrary units) corresponding to this interpretation are $A_4$ for the peak designated +4, $A_3$ for the peak designated +3, $A_2$ for the peak designated +2, and $A_1$ for the peak designated +1. In this instance, the sum of the intensities of all the first order products for the candidate charge state of +4 is $\Sigma A_i + 4 = A_4 + A_3 + A_2 + A_1$. Similarly, for the candidate charge state of a first order ion product of +3, if the intensity of peaks (in arbitrary units) corresponding to this interpretation $B_3$ for the peak designated +3, $B_2$ for the peak designated +2, and $B_1$ for the peak designated +1. Thus the sum of the intensities of all the first order products for the candidate charge state of +3 is $\Sigma B_i + 3 = B_3 + B_2 + B_1$ Likewise, for the candidate charge state of a first order ion product of +2, if the intensity of peaks (in arbitrary units) corresponding to this interpretation $C_2$ for the peak designated +2, and $C_1$ for the peak designated +1. In this instance, the sum of the intensities of all the first order products for the candidate charge state of +2 is $\Sigma C_i + 2 = C_2 + C_1$. Having acquired this information, if $\Sigma B_i + 3 >> \Sigma C_i + 2$, and $\Sigma B_i + 3 >> \Sigma A_i + 4$, if a Chebychev inequality is applied, it will be apparent that $\Sigma B_i + 3$ is the most likely charge state for the first order product.

Other steps may include for example, analysis comprising utilizing corresponding first order ion products in product data over the same spectral range, from a different charge state of the precursor ion generated from a different scan to indicate possible candidate charge states. This step is discussed in greater detail with respect to FIG. 11 below.

Steps 305, 310, 320, 330, and 340 have only briefly been addressed above, but implementation of these analysis techniques should be known to those skilled in the art, and will become clearer when FIGS. 6-11 are discussed below.

It will be apparent that FIG. 4 is similar to FIG. 3, in that the same steps are illustrated for the determination of the candidate first order ion products, but in this instance the analysis steps are carried out sequentially, and after the result of each analysis step has been acquired, the candidate charge state(s) of the first order ion product can be determined. Similarly, FIG. 5 is similar to FIGS. 3 and 4, in that the same steps are illustrated for the determination of the candidate first order ion products, but in this instance, although each step is carried out sequentially, it may be possible to determine the candidate charge state(s) of the first order ion product after the first analysis step 305 alone, in which case the remaining analysis steps 310, 320, 330 and 340 need not be run. Alternatively it may only be necessary to run two, three or four of the analysis steps before the user is able to determine the candidate charge states of the first order ion products. In the alternative, it may be necessary to run all analysis steps.

FIGS. 6-11 illustrate how the invention can be utilized to determine the candidate charge states of the first order ion products, and hence enable and improve the peptide searching capabilities.

Figure 6:
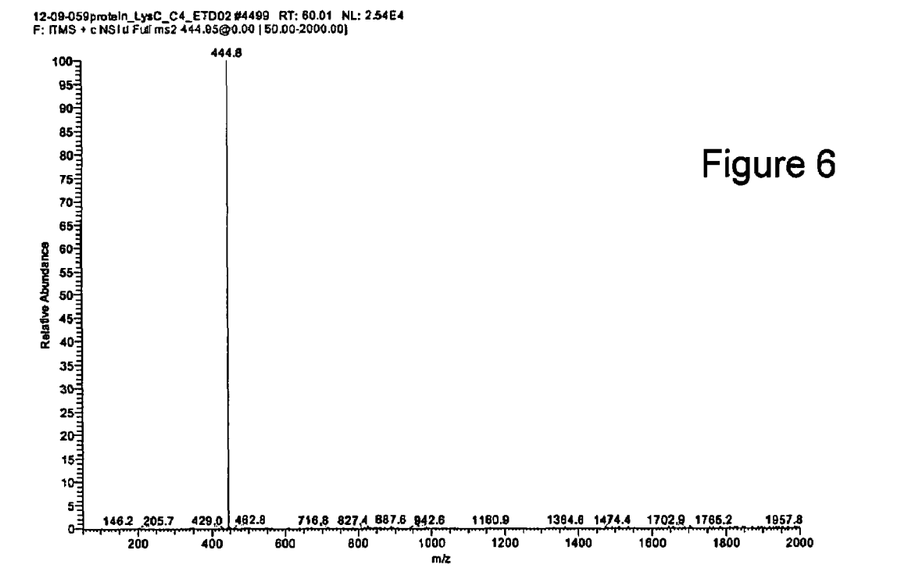
FIG. 6 illustrates experimental product ion spectral data, and shows ion product data that is below a threshold value, according to an aspect of the present invention.

FIG. 6 shows the mass-to-charge ratio spectral data obtained after fragmentation of a 444.95 (m/z) precursor ion by the ETD process. This is an example of a low quality spectrum, a spectrum in which only one distinct and significant peak can be observed at 444.8 (m/z). The other peaks that have (m/z) identifications on the spectral data plot are below the threshold value, and considered to be "noise" and to contain no "useful" information with respect to the first order ion products and hence the precursor ion.

Figure 7:
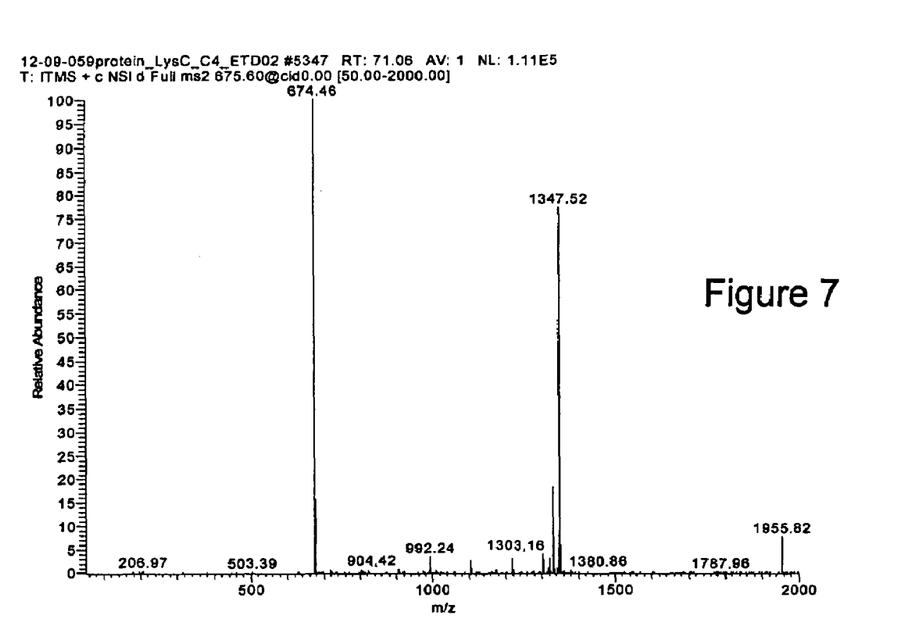

FIG. 7 shows the mass-to-charge ratio spectral data obtained after fragmentation of a 675.60 (m/z) precursor ion by the ETD process. In this spectrum, two distinct and significant peaks can be observed at 674.46 and 1347.52 (m/z). There are other peaks that have (m/z) identifications on the spectral data plot, some of which are below the threshold value, and considered to be "noise" and to contain no "useful" information with respect to the first order ion products and hence the precursor ion, but others such as 992.24 and 1303.16 (m/z) that may be considered useful. However, in this example, the one peak at 674.46 (m/z) would be assigned a +2 charge and the peak at 1347.52 (m/z) would be assigned a +1 charge. All other candidate charge states except +2 for the first order ion product would be excluded in the spectrum, as there are no significant peaks larger than the proposed mass for the +2 charge. This mass-to-charge ratio spectral representation is considered a typical spectrum that results after ETD fragmentation for a +2 charged first order product ion. It would not be necessary to carry out any further analysis to determined possible candidate charge states of the first order ion products in this example, it would be apparent from the data attained.

Figure 8:
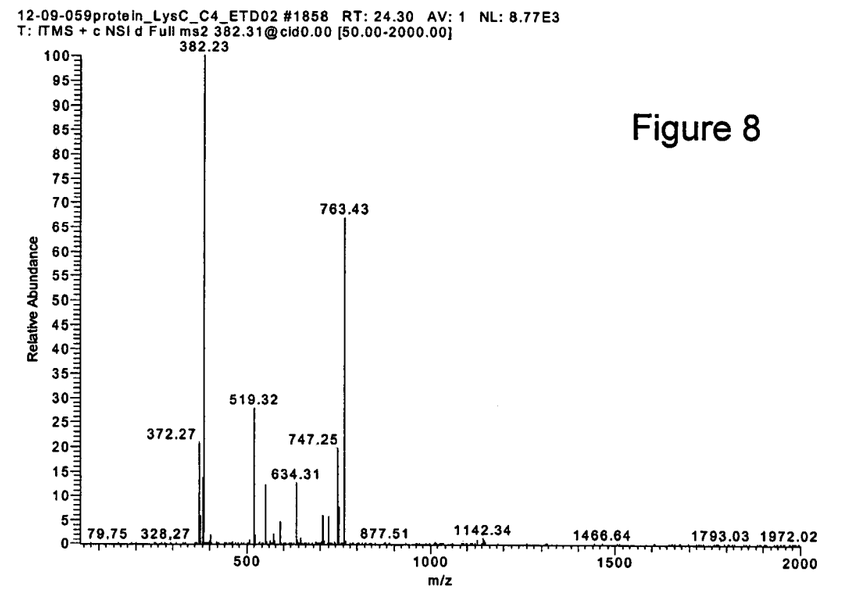
FIG. 8 illustrates experimental product ion spectral data, and shows that charge states above +3 can be excluded since there are no peaks above 1142 amu, according to an aspect of the present invention.

FIG. 8 shows the mass-to-charge ratio spectral data obtained after fragmentation of a 382.31 (m/z) precursor ion by the ETD process. In this spectrum, several distinct and significant peaks can be observed, including those at 382.23 and 76.43 (m/z). In this example, charge states higher than +3 are excluded as candidates since there are no significant peaks greater than 1142 (m/z). The candidate charge states for the first order in products could be +2 or +3 based on the significant peaks alone. However, the step 205 is utilized to further analyze the data, it can be observed that there is a peak adjacent the 382.23 (m/z) peak, which may represent a 8-9 amu loss from a +2 charged first order ion product. There is also a peak adjacent the 763.43 (m/z) peak, which may represent a 16-18 amu loss from a +1 charged first order ion product. From this information, the candidate charge state for the first order ion product would be +2.

Figure 9:
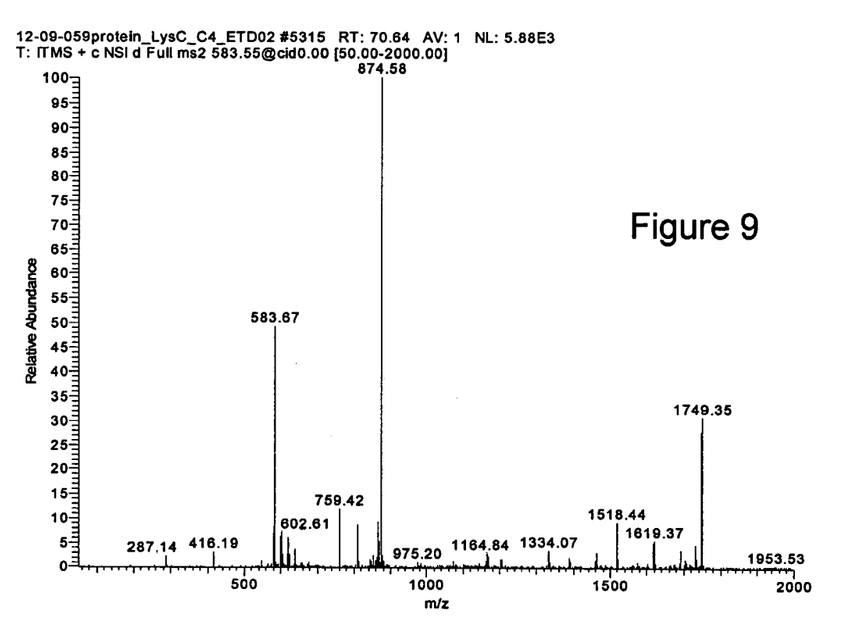
FIG. 9 illustrates experimental product ion spectral data, and shows that the candidate charge states are +3 and +6, but that the +3 charge state should be assigned, according to an aspect of the present invention.

FIG. 9 shows the mass-to-charge ratio spectral data obtained after fragmentation of a 583.55 (m/z) precursor ion by the ETD process. In this spectrum a first possible interpretation of the data would be that the 583.67 (m/z) peak represent the +3 charge state, the 874.58 (m/z) peak represent the +2 charge state and the 1749.35 (m/z) peak represent the +1 charge state. This would be consistent with the expectation held by those skilled in the art that for the +3 charge state the +1, +2 and +3 first order ion products will normally have the tallest peaks in the spectrum. However, a second possible interpretation dictates that the +6 charge state is in principle possible since the peak at 1164.84 (m/z) could be the +3 charge state. However, if this were the case, then the peak at 874.58 (m/z) would be the +4 charge state. To those skilled in the art, it will be apparent that this interpretation is unlikely since for the +6 charge state, the +3 and the +4 charge states do not normally demonstrate high intensities, in particular the +4 peak. In this example it can be seen that the 874.58 (m/z) peak is in fact the maximum peak size across the entire spectral range and therefore the first interpretation is the one that would be assigned, +3 for the 583.67 (m/z) peak.

Figure 10:
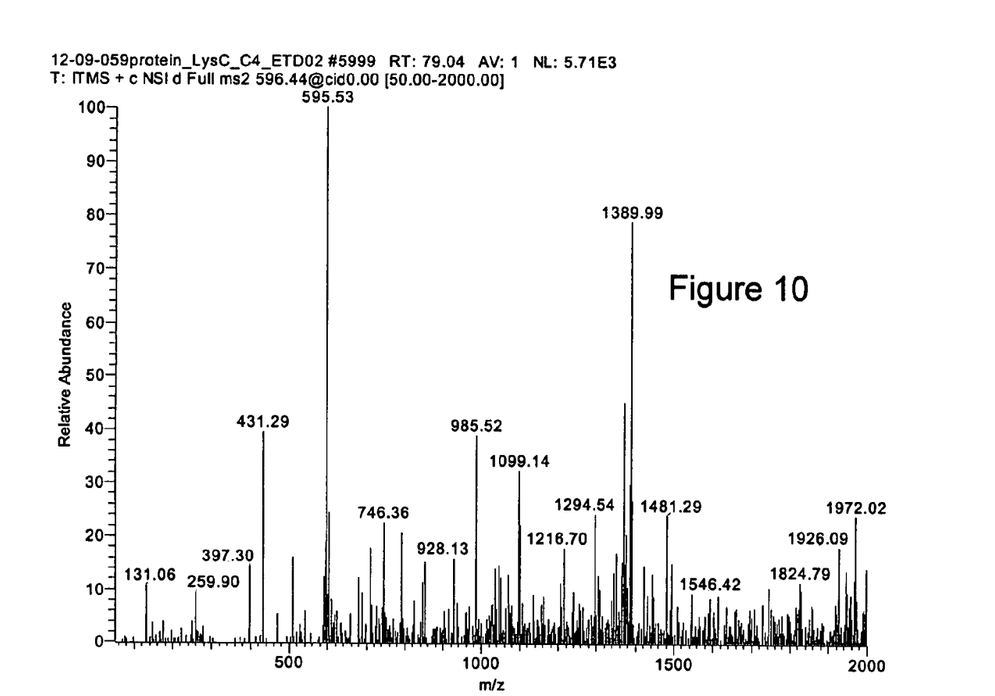
FIG. 10 illustrates experimental product ion spectral data, and shows that the charge state of +7 should be assigned, according to an aspect of the present invention.
Figure 11:
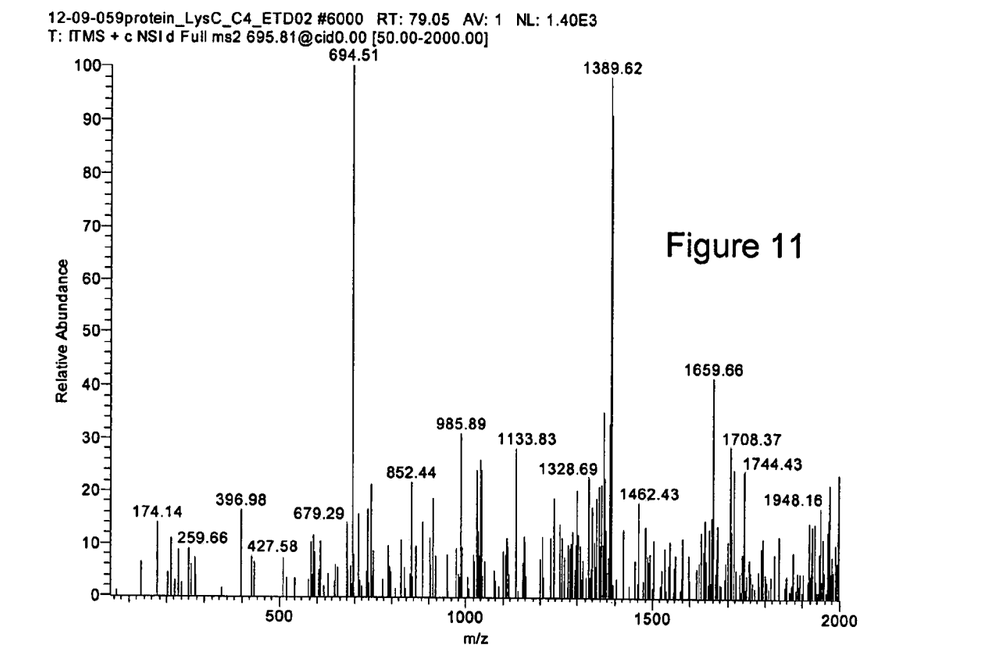
FIG. 11 illustrates experimental product ion spectral data, and shows that the charge state of +6 should be assigned, according to an aspect of the present invention.

FIGS. 10 and 11 show the mass-to-spectral data obtained after fragmentation of 596.44 amu and 695.81 (m/z) precursor ions respectively, by the ETD process. Taking FIG. 10 first, if the charge state of +7 is considered as a candidate charge state for the first order ion product identified as the peak appearing at 595.53 (m/z), then it can be deduced that the peak appearing at 1389.99 (m/z) is the +3 peak. There is a peak that appears at around 833 (m/z) that could be the +5 peak, but the +4 and +6 peaks do not appear to exist in this particular scan. In particular, the peak that should represent the +6 charge state at 694 (m/z) is missing. However, by comparing complementary information from another spectrum, for example that shown in FIG. 10, the charge states for the two different scans can be ascertained with a certain degree of certainty. Looking at FIG. 11, it will be apparent that both spectra share several common peaks, for example peaks at 1389 (m/z) and 985 (m/z). In addition, it can be seen that in FIG. 10, there is a peak at 694 (m/z). From the complementary information from these two spectra, one is able determine the candidate charge states of the first order ion products illustrated. Considering the information above, one is able to determine that the candidate charge state for the 595 (m/z) peak in FIG. 10 is +7, and the candidate charge state for the 694 (m/z) peak in FIG. 11 is +6.

Although various exemplary aspects of the invention have been disclosed, it should be apparent to those skilled in the that various changes and modifications can be made without departing from the scope of the present invention, and incorporating some, if not all the advantages discussed above. These and other modifications are intended to be within the scope of the present invention.

What is claimed is:

1. A method of analyzing product ion data for use in peptide sequence determination by searching a database for matches to mass spectra, the method comprising:
    (a) subjecting a precursor ion of a sample having a peak abundance to fragmentation by Electron Transfer Dissociation (ETD) to generate ion product data over a spectral range;
    (b) determining the ion product data quality and utilizing only ion product data of at least a predetermined quality, if any, for further processing in subsequent steps;
    (c) identifying peaks of the ion product data of the at least predetermined quality that represent first order ion products and higher order ion products, wherein the first order ion products comprise one or more members of the group consisting of charge reduced precursors, electron transfer products anion adducts, side chain losses and hydrogen transfer products and wherein the higher order ion products comprise at least one ion product resulting from a dissociation reaction of a first order ion product;
    (d) utilizing the ion product data of the at least predetermined quality and the identified peaks of the first and higher order ion product data to determine candidate charge states of the first order ion products; and
    (e) submitting the identified peaks and the determined candidate charge states to a nucleotide sequence database searching program for performing the peptide sequence determination.

2. The method of claim 1, further comprising:
    (d1) assigning a probability score to each of the candidate charge states prior to the submitting step (e) such that the nucleotide sequence database searching program performs searches of the database utilizing the candidate charge states in order of their respective probability scores.

3. The method of claim 2, further comprising:
    (d2) utilizing the probability score to identify a probable precursor ion prior to the submitting step (e).

4. The method of claim 1, wherein:
    the step (c) of identifying peaks of the ion product data of the at least predetermined quality that represent first order ion products and higher order ion products comprises utilizing mass-to-charge ratio intervals between spectral peaks of the ion product data.

5. The method of claim 1, wherein:
    the quality of all the ion product data determined in step (b) is below a threshold value and the ion product data is used to ascertain that the candidate charge state corresponding to an observed peak of the ion product data is +2.

6. The method of claim 1, wherein:
    the quality of all the ion product data determined in step (b) is below a threshold value and it is determined that the ion product data is not useful for peptide sequencing purposes.

7. The method of claim 1, wherein:
    the step (b) of determining the ion product data quality comprises comparing peak abundances of the ion product data to a threshold value, said threshold value being 0.0001 percent of the precursor ion peak abundance.

8. The method of claim 1, wherein:
    the step (b) of determining the ion product data quality comprises determining a number of spectral peaks of the ion product data occurring over half the spectral scan range.

9. The method of claim 1, wherein:
    the step (b) of determining the ion product data quality comprises determining a number of spectral peaks of the ion product data occurring over the whole spectral scan range.

10. The method of claim 1, wherein:
    the higher order ion products comprise one or more members of the group consisting of fragment ions, products of fragment ion adducts and products of fragment ion neutral losses.

11. The method of claim 1, wherein the step (d) of utilizing the ion product data of the at least predetermined quality and the identified peaks of the first and higher order ion product data to determine candidate charge states of the first order ion products comprises:
    determining at least one candidate state charge state by identifying complementary second order ion products and applying a Fast Fourier Transform to the complementary second order data.

12. The method of claim 1, further comprising:
    (c1) determining, after step (c), a the ratio of the first to higher order ion products; and
    (c2) excluding the ion product data from further processing in subsequent steps if the ratio of the first to higher order ion products less than a predetermined threshold.

13. The method of claim 1, wherein the step (d) of utilizing the ion product data of the at least predetermined quality and the identified peaks of the first and higher order ion product data to determine candidate charge states of the first order ion products comprises:
    identifying neutral loss ion peaks adjacent to peaks representing the first order ion products to distinguish between and test for presence of +1 and +2 first order ion products and higher charge state first order ion products.

14. The method of claim 1, wherein the step (d) of utilizing the ion product data of the at least predetermined quality and the identified peaks of the first and higher order ion product data to determine candidate charge states of the first order ion products comprises:

analyzing the densities of peaks corresponding to higher order ion products between peaks corresponding to first order ion products to distinguish between different candidate charge state values.

15. The method of claim 1, wherein the step (d) of utilizing the ion product data of the at least predetermined quality and the identified peaks of the first and higher order ion product data to determine candidate charge states of the first order ion products comprises:

utilizing intensity ratios of spectral peaks of the ion product data to distinguish between a possible higher and a possible lower candidate charge state.

16. The method of claim 1, wherein the step (d) of utilizing the ion product data of the at least predetermined quality and the identified peaks of the first and higher order ion product data to determine candidate charge states of the first order ion products comprises:

utilizing other corresponding ion product data in addition to the ion product data to indicate possible candidate charge states, wherein the other corresponding ion product data is obtained over a same spectral range and from the same sample as the ion product data and comprises a peak of another precursor ion having a different charge state from the precursor ion.

17. The method of claim 1, wherein the step (d) of utilizing the ion product data of the at least predetermined quality and the identified peaks of the first and higher order ion product data to determine candidate charge states of the first order ion products comprises:

ranking a plurality of sums of intensities of identified peaks of first order ion products, each of said sums of the form $$\sum_{i=1}^{n} A_i^n$$

wherein n is a possible candidate charge state for a particular first order ion product and $A_i^n$ is the intensity of an identified peak of another first order ion product that has possible candidate charge state i when the particular first order ion product has charge state n, and utilizing an appropriate filter to evaluate the ranking.

18. The method of claim 17, wherein:

the appropriate filter is a Chebyshev inequality.

19. The method of claim 1, wherein the step (d) of utilizing the ion product data of the at least predetermined quality and the identified peaks of the first and higher order ion product data to determine candidate charge states of the first order ion products comprises:

summing intensities of the identified peaks of the ion product data corresponding to possible candidate first order ion products.

20. The method of claim 1, wherein the step (d) of utilizing the ion product data of the at least predetermined quality and the identified peaks of the first and higher order ion product data to determine candidate charge states of the first order ion products comprises:

(d1) performing at least two charge state analyses simultaneously; and (d2) combining the results of the at least two charge state analyses to determine candidate charge states of the first order ion products, wherein the performing of each of the at least two charge state analyses is chosen from the group consisting of: (I) determining at least one candidate state charge state by identifying complementary second order ion products and applying a Fast Fourier Transform to the complementary second order data, (II) identifying neutral loss ion peaks adjacent to peaks representing the first order ion products to distinguish between and test for presence of +1 and +2 first order ion products and higher charge state first order ion products, (III) analyzing the densities of peaks corresponding to higher order ion products between peaks corresponding to first order ion products to distinguish between different candidate charge state values, (IV) utilizing intensity ratios of peaks of the ion product data to distinguish between a possible higher candidate charge state and a possible lower candidate charge state, and (V) ranking the intensities of peaks of the ion product data corresponding to each of a plurality of possible candidate charge states for the first order ion products, and utilizing an appropriate filter.

21. The method of claim 1, wherein the step (d) of utilizing the ion product data of the at least predetermined quality and the identified peaks of the first and higher order ion product data to determine candidate charge states of the first order ion products comprises:

(d1) performing a first charge state analysis;

(d2) determining, from the results of the first charge state analyses; if another charge state analysis must be performed;

(d3) performing another charge state analysis, different from all prior charge state analyses, if the determination of step (d2) indicates that another analysis must be performed;

(d4) determining, from the results of all prior charge state analyses; if another charge state analysis must be performed; and (d5) repeating steps (d3) and (d4) until the determination made in the most recent execution of step (d3) indicates that another charge state analysis need not be performed or until the number of repetitions of steps (d3) and (d4) has reached a predetermined limit, wherein the performing of each charge state analysis is chosen from the group consisting of: (I) determining at least one candidate state charge state by identifying complementary second order ion products and applying a Fast Fourier Transform to the complementary second order data, (II) identifying neutral loss ion peaks adjacent to peaks representing the first order ion products to distinguish between and test for presence of +1 and +2 first order ion products and higher charge state first order ion products, (III) analyzing the densities of peaks corresponding to higher order ion products between peaks corresponding to first order ion products to distinguish between different candidate charge state values, (IV) utilizing intensity ratios of peaks of the ion product data to distinguish between a possible higher candidate charge state and a possible lower candidate charge state, and (V) ranking the intensities of peaks of the ion product data corresponding to each of a plurality of possible candidate charge states for the first order ion products, and utilizing an appropriate filter.

22. A method of analyzing product ion data for use in peptide sequence determination by searching a database for matches to mass spectra, the method comprising:

(a) subjecting a precursor ion with a peak abundance to fragmentation by Electron Capture Dissociation (ECD) to generate product ion data over a spectral range;

(b) determining the ion product data quality and utilizing only ion product data of at least a predetermined quality, if any, for further processing, in subsequent steps;

(c) identifying peaks of the ion product data of the at least predetermined quality that represent first order ion products and higher order ion products;

(d) utilizing the ion product data of the at least predetermined quality and the identified peaks of the first and higher order ion product data to determine, by at least two different charge state analyses, tentative candidate charge states of the first order ion products;

(e) combining the results of the at least two different charge state analyses to determine candidate charge states of the first order ion products; and (f) submitting the identified peaks and the determined candidate charge states to a nucleotide sequence database searching program for performing the peptide sequence determination.

23. The method of claim 22, wherein:

wherein each of the at least two charge state analyses is chosen from the group consisting of: (I) determining at least one candidate state charge state by identifying complementary second order ion products and applying a Fast Fourier Transform to the complementary second order data, (II) identifying neutral loss ion peaks adjacent to peaks representing the first order ion products to distinguish between and test for presence of +1 and +2 first order ion products and higher charge state first order ion products, (III) analyzing the densities of peaks corresponding to higher order ion products between peaks corresponding to first order ion products to distinguish between different candidate charge state values, (IV) utilizing intensity ratios of peaks of the ion product data to distinguish between a possible higher candidate charge state and a possible lower candidate charge state, and (V) ranking the intensities of peaks of the ion product data corresponding to each of a plurality of possible candidate charge states for the first order ion products, and utilizing an appropriate filter.

24. A storage medium encoded with machine-readable computer program code for analyzing product ion data for use in peptide sequence determination by searching a database for matches to mass spectra, the storage medium including instructions for:

(a) obtaining ion product data over a spectral range, the ion product data having been generated by Electron Transfer Dissociation (ETD);

(b) determining the ion product data quality and utilizing only ion product data of at least a predetermined quality, if any, for further processing;

(c) identifying peaks of the ion product data of the at least predetermined quality that represent first order ion products and higher order ion products, wherein the first order ion products comprise one or more members of the group consisting of charge reduced precursors electron transfer products, anion adducts, side chain losses and hydrogen transfer products and wherein the higher order ion products comprise at least one ion product resulting from a dissociation reaction of a first order ion product;

(d) utilizing the ion product data of the at least predetermined quality and the identified peaks of the first and higher order ion product data to determine candidate charge states of the first order ion products; and (e) submitting the identified peaks and the determined candidate charge states to a nucleotide sequence database searching program for performing the peptide sequence determination.

* * * * *

UNITED STATES PATENT AND TRADEMARK OFFICE
CERTIFICATE OF CORRECTION

PATENT NO. : 7,595,485 B1
APPLICATION NO. : 11/703941
DATED : September 29, 2009
INVENTOR(S) : Sadygov et al.

It is certified that error appears in the above-identified patent and that said Letters Patent is hereby corrected as shown below:

Claim 1, column 13, line 49
replace "transfer products anion adducts"
with --transfer products, anion adducts--

Claim 12, column 14, line 52
replace "after step (c), a the ratio of"
with --after step (c), a ratio of--

Signed and Sealed this

Twenty-seventh Day of April, 2010

David J. Kappos
*Director of the United States Patent and Trademark Office*